(12) United States Patent
Binner

(10) Patent No.: US 12,358,008 B2
(45) Date of Patent: *Jul. 15, 2025

(54) DEVICE FOR SUPPLYING A COMPOSITION TO A PRESSURIZED DEPOSITION SYSTEM

(71) Applicant: Johnson & Johnson Consumer Inc., Skillman, NJ (US)

(72) Inventor: Curt Binner, Furlong, PA (US)

(73) Assignee: Kenvue Brands LLC, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,260

(22) Filed: Jan. 6, 2023

(65) Prior Publication Data

US 2023/0149958 A1 May 18, 2023

Related U.S. Application Data

(63) Continuation of application No. 16/746,214, filed on Jan. 17, 2020, now Pat. No. 11,548,019.

(Continued)

(51) Int. Cl.
*B05B 9/08* (2006.01)
*B05B 7/24* (2006.01)
(Continued)

(52) U.S. Cl.
CPC .......... *B05B 9/0838* (2013.01); *B05B 12/008* (2013.01); *B05B 12/081* (2013.01); *B05B 12/085* (2013.01); *B05B 7/2467* (2013.01)

(58) Field of Classification Search
CPC ... B05B 9/0838; B05B 12/008; B05B 12/081; B05B 12/085; B05B 7/2467
See application file for complete search history.

(56) References Cited

U.S. PATENT DOCUMENTS 3,346,195 A 10/1967 Groth
3,974,998 A * 8/1976 Wood ..................... B05B 9/03
137/594

(Continued)

FOREIGN PATENT DOCUMENTS

CN 107552291 A 1/2018
DE 102007011909 3/2008

(Continued)

OTHER PUBLICATIONS

Search Report dated Sep. 27, 2022 issued in corresponding Singapore patent application No. 11202107037P.

(Continued)

*Primary Examiner* — Steven M Cernoch
(74) *Attorney, Agent, or Firm* — Wan Chich Lee; Haug Partners LLP

(57) ABSTRACT

A device for dispensing a fluid topical composition includes a reservoir storing the composition and dispensing a pressurized flow of the composition. The device also includes an accumulator having an expandable chamber in fluidly communication with the reservoir. The chamber is biased towards a deflated configuration so that, when filled with the composition the chamber expands against this bias applying pressure to the composition stored therein. The device includes a supply valve regulating the flow of the composition from the reservoir to the accumulator, and a pressure sensor. The device further includes a processing arrangement analyzing data from the sensor to determine whether pressure in the accumulator is above a predetermined threshold and controlling the supply valve to maintain the pressure within a desired pressure range. The device also includes a deposition arrangement dispensing the composition from the accumulator under control of the processing arrangement.

22 Claims, 4 Drawing Sheets

Related U.S. Application Data

(60) Provisional application No. 62/798,745, filed on Jan. 30, 2019.

(51) Int. Cl.
  *B05B 12/00*   (2018.01)
  *B05B 12/08*   (2006.01)

(56) References Cited

U.S. PATENT DOCUMENTS

| | | | |
|---|---|---|---|
| 11,548,019 B2 * | 1/2023 | Binner | B05B 12/081 |
| 2005/0021005 A1 | 1/2005 | Flaherty et al. | |
| 2005/0172956 A1 | 8/2005 | Childers | |
| 2012/0219699 A1 * | 8/2012 | Pettersson | B05B 12/124 |
| | | | 427/8 |
| 2015/0166253 A1 | 6/2015 | Nomura et al. | |

FOREIGN PATENT DOCUMENTS

| | | |
|---|---|---|
| EP | 1452199 | 9/2004 |
| EP | 1563865 | 8/2005 |
| GB | 2 326 609 A | 12/1998 |
| JP | 2001232245 A | 8/2001 |
| JP | 2018511355 | 4/2018 |
| RU | 177 849 U1 | 3/2018 |
| WO | WO 2004/043533 A2 | 3/2004 |
| WO | 2016/185163 | 11/2016 |

OTHER PUBLICATIONS

Written Opinion dated Sep. 29, 2022 issued in corresponding Singapore patent application No. 11202107037P.
Written Opinion dated Jul. 26, 2022.
Search Report dated Jun. 15, 2023 from Russian patent application No. 2021125210.
Preliminary Office Action and English translation of Brazilian Patent Application No. BR1120210147101 dated May 13, 2025.

* cited by examiner

DEVICE FOR SUPPLYING A COMPOSITION TO A PRESSURIZED DEPOSITION SYSTEM

PRIORITY CLAIM

This application is a continuation of U.S. patent application Ser. No. 16/746,214 filed Jan. 17, 2020, which claims priority to U.S. Provisional Application Ser. No. 62/798,745 filed Jan. 30, 2019, the entire contents of each of the applications identified above are hereby incorporated by reference herein.

FIELD OF INVENTION

The present invention relates to devices and methods for applying a composition onto a keratinous surface, e.g., a person's skin. More specifically, the invention relates to devices and methods for applying a pressurized topical composition (e.g., a cosmetic composition or a skin treatment composition) to enhance the aesthetic appearance of skin.

BACKGROUND

Topical compositions having a variety of different forms, e.g., powder, liquid, viscous fluid, pressed compact, etc., may be applied to a keratinous surface, such as the skin of a user, to impart a desired benefit. In particular, the composition may be applied to the skin of the user to impart an improved aesthetic appearance to the skin. The composition may be applied to desired regions of the skin in a variety of different ways. For example, powdered compositions may be applied to the skin by manually transferring the composition via a brush. A viscous fluid composition, such as a liquid foundation composition, may be applied to the skin by manually distributing and smearing across a large area of the keratinous surface the composition with the user's fingers or a sponge.

SUMMARY OF THE INVENTION

One exemplary embodiment of the present invention is directed to a handheld device. The device comprising a reservoir configured to store a fluid topical composition and to dispense a pressurized flow of the composition. The device also comprises an accumulator including an expandable chamber in fluidly communication with the reservoir. The expandable chamber is biased towards a deflated configuration so that, when filled with the composition the chamber expands against this bias applying pressure to the composition stored therein. The device further comprises a supply valve between the reservoir and the accumulator regulating the flow of the composition from the reservoir to the accumulator, and a pressure sensor generating pressure data corresponding to a pressure of the composition in the accumulator. The device also includes a processing arrangement receiving the pressure data from the pressure sensor, analyzing the pressure data to determine whether the pressure in the accumulator is above a predetermined threshold value and controlling the supply valve to maintain the pressure of the accumulator within a range between the predetermined threshold value and a predetermined ceiling value. In addition, the device comprises a deposition arrangement fluidly connected to an outlet of the accumulator and dispensing the composition from the accumulator under control of the processing arrangement.

A method for dispensing a topical composition is also described. The method comprises supplying, via a supply valve, a pressurized flow of the composition to an accumulator including an expandable chamber therein. The expandable chamber is biased towards a deflated configuration so that, when filled with the composition the chamber expands against this bias applying pressure to the composition stored therein. The method also comprises generating, by a pressure sensor, pressure data corresponding to a pressure of the composition in the accumulator. The method further comprises analyzing, by a processing arrangement, the pressure data received from the pressure sensor to determine whether the pressure in the accumulator is above a predetermined threshold value and to control the supply valve to maintain the pressure of the accumulator within a range between the predetermined threshold value and a predetermined ceiling value. The method further comprises dispensing, by a deposition arrangement fluidly connected to an outlet of the accumulator, the composition from the accumulator under control of the processing arrangement.

A method for purging fluid from air-exposed regions of a topical sprayer is also provided. The method comprises supplying, via a supply valve, a pressurized flow of a topical composition to an accumulator including an expandable chamber therein. The expandable chamber is biased towards a deflated configuration so that, when filled with the composition the chamber expands against this bias applying pressure to the composition stored therein. The method also comprises generating, by a pressure sensor, pressure data corresponding to a pressure of the composition in the accumulator. The method further comprises analyzing, by a processing arrangement, the pressure data received from the pressure sensor to determine whether the pressure in the accumulator is above a cleaning threshold value and to control the supply valve to maintain the pressure of the accumulator above the cleaning threshold value. The method further comprises dispensing, by a deposition arrangement fluidly connected to an outlet of the accumulator, the composition from the accumulator under control of the processing arrangement until the pressure in the accumulator falls below a predetermined ceiling value. The cleaning threshold value is higher than the predetermined ceiling value. The cleaning threshold value is also selected such that the deposition arrangement dispenses the composition from the accumulator at a pressure that provides force sufficient to dislodge obstructions in the deposition arrangement.

These and other aspects of the invention will become apparent to those skilled in the art after a reading of the following detailed description of the invention, including the figures and appended claims.

DETAILED DESCRIPTION

The present application provides a device and method for applying a pressurized composition to a keratinous substrate, e.g., a surface of the skin. In particular, the device of the present application controls delivery of a pressurized fluid composition to the keratinous substrate and is capable of being used while the device is held in any orientation, including an inverted orientation. Embodiments of the device receive a supply of the composition having a high initial pressure and dispense the composition at a reduced pressure suitable for application to a biologic surface, such as, for example, the skin of the face (e.g., suitably pressured to be tolerable to the person without significant pain during use or damage to the skin). The reduced pressure may also be selected to be suitable for dispensing the composition to form a thin layer of the composition on the skin. Preferably, the reduced pressure is selected to more controllably dispense the composition in a thin layer onto a desired area of skin as compared to higher pressures. The pressure may be selected to dispense the composition in a plurality of pulses such that the layer of composition formed on the substrate from each pulse covers a suitably sized area that repeated dispensing of pulses of the composition across the substrate allows for detailed and controlled application of the composition. For example, repeated dispensing of pulses of the composition across the skin allows for detailed and controlled application of a cosmetic composition to impart an aesthetically pleasing look. The devices and methods of the present invention may also be directed to applying a pressurized composition onto biologic surfaces other than a person's skin. Other applications include, but are not limited to, applying a pressurized composition to the teeth or eyes, or to mucous membranes near the eyes and ears, or inside the nose, mouth, lip, vagina, the urethral opening or the anus of the person.

Figure 1:
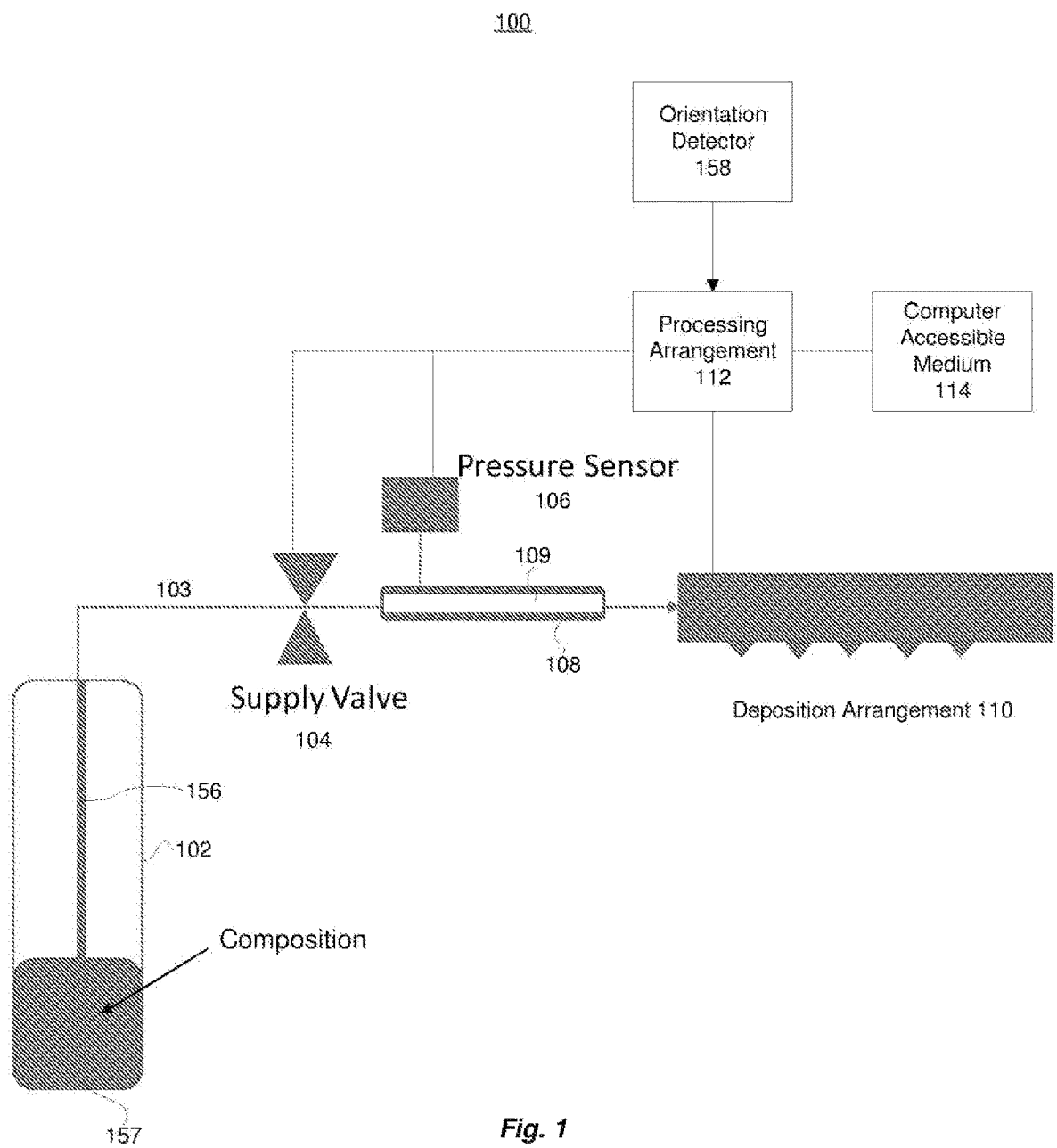
FIG. 1 shows a block diagram of an exemplary device for applying a composition to the skin of a user, according to an exemplary embodiment of the present application.

FIG. 1 shows a diagram of an exemplary device 100 for applying a fluid composition, e.g., a fluid skin treatment composition or a fluid cosmetic composition, to a keratinous substrate such as skin. The device 100 of this embodiment is sized and shaped to be a handheld device designed to be held within a palm of a user's hand.

The fluid composition may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean *Glycine soja* oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, tales and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavonoids, Licorice root extract, Mulberry root extract, *Dioscorea* Coposita root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol, phenylethyl resorcinol, 1-(2,4-dihydroxyphenyl)-3-(2,4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "*Tanacetum parthenium*," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, *Picia anomala*, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc mutate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T ISO), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, *Chamomilla* extract, allantoin, opacifiers, tales and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea* Coposita root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkyl-resorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

In some preferred embodiments, useful benefit agents for acne include, but are not limited, salicylic acid, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean *Glycine soja* oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

In an exemplary embodiment, the fluid composition may be a suspension containing particulate materials therein, preferably, the particulates are uniformly distributed and/or suspended in a suitable topical carrier. For example, the fluid composition may comprise a topical carrier and particulates such as, for example, reflectance modifying agents (RMAs) (any component useful for altering reflectance of the skin) e.g., pigments and/or high refractive index particles for modifying a reflectance of skin. In particular, the high refractive index particles may comprise particles having a refractive index of 2.0 or greater. In one specific example, the RMA may comprise particles of titanium dioxide. The RMA may comprise or consist of particles of having an average diameter from about 0.35 microns to about 1.35 microns, from about 0.5 microns to about 1.0 microns, or from about 0.6 microns to about 0.8 microns. In one example, the RMA may comprise or consist of particles of having an average diameter of about 0.76 microns. In another example, the RMA may comprise or consist of particles having a distribution of particle sizes with a median diameter at about 0.58 microns. In one example, the RMA may comprise or consist of particles of having a distribution of particle sizes as follows: less than 10% of the particles having a diameter about or less than 0.37 microns, less than 50% of the particles having a diameter about or less than 0.58 microns, and less than 90% of the particles having a diameter about or less than 1.31 microns. Specifically, the particles may be uniformly distributed and/or suspended in the topical composition (e.g., a liquid suspension). It is contemplated that the fluid composition may have any suitable viscosity for a topical formulation suitable for use on the skin. The fluid composition may, for example, be a thin liquid or a thick viscous fluid. The viscosity of the fluid composition may be selected to be sufficiently viscous to allow particulate materials contained in the fluid composition to remain suspended over a shelf life of the composition and thereby improve stability of the composition during storage, while being sufficiently thin such that the composition can be easily atomized into fine droplets for deposition onto the skin. For example, the fluid composition may have a viscosity at room temperature from about 1 cP to about 1200 cP, about 5 cP to about 1000 cP, or about 8 cP to about 882 cP. In some examples, the fluid composition may have a viscosity at room temperature below about 300 cP.

The device 100 according to this embodiment comprises a reservoir 102 holding a supply of the fluid composition to be dispensed by the device 100. The reservoir 102 in this embodiment includes a storage chamber charged with a pressurized supply of the composition therein although, as would be understood by those skilled in the art, multiple storage containers may also be provided, for example, if the composition to be applied is more effective when multiple components are mixed immediately before application. For example, the reservoir 102 may initially be charged with a supply of the composition, and as the device 100 applies the composition to the skin, the amount and/or pressure of the supply contained in the reservoir 102 gradually diminishes. In some embodiments, the reservoir 102 is a removeable container that can be replaced upon exhaustion of one or more of the contents therein.

Figure 2:
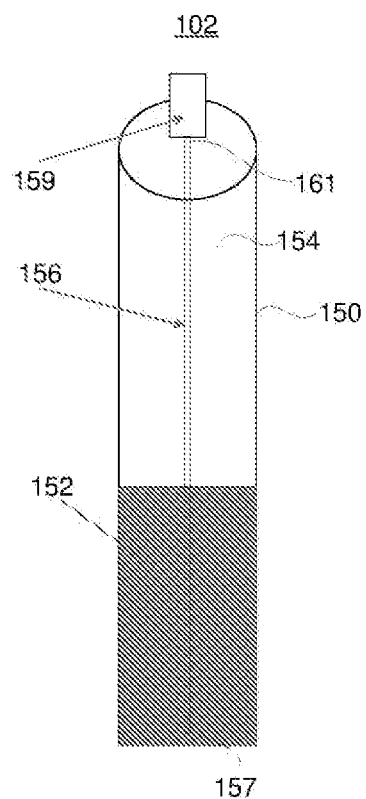
FIG. 2 shows an exemplary embodiment of a reservoir charged with the composition that can be used with the exemplary device shown in FIG. 1.

In one exemplary embodiment, as shown in FIG. 2, the reservoir 102 comprises a rigid container defining a storage chamber 150 therein for holding the composition 152 and a propellant 154, and a dispenser 159, e.g., a valve or nozzle, for dispensing a pressurized flow of the composition 152 when the device is activated. The storage chamber 150 in this embodiment is rigid and does not vary in size or change shape as the pressure within the chamber 150 changes over time (i.e., as the composition is dispensed). For example, the storage chamber 150 may have a volume of about 30 mL or less, about 20 mL or less, or about 15 mL or less. The storage chamber 150 may be charged with any suitable amount of the composition 152, such as, for example, about 10 mL or less, about 8 mL or less, or about 5 mL or less of the composition 152, and propellant 154. More particularly, the reservoir 102 may be any suitable canister having an interior surface that does not cause undesirable interactions between the composition 152 and the canister. For example, the reservoir 102 may be a metal aerosol canister, and preferably, an aluminum aerosol canister, coated with a continuous film of a protective coating that does not react with the composition 152. The film creates a barrier preventing undesirable interactions between the composition 152 and the canister (e.g., formation of grey color aluminum oxide particulates from the aluminum canister that can discolor the composition 152). The protective coating may be a polymer coating, for example, an epoxy-phenolic coating as would be understood by those skilled in the art.

The propellant 154 in the storage chamber 150 pressurizes the composition 152 to generate propulsion for dispensing a pressurized flow of the composition 152 from the storage chamber 150 when the dispenser 159 is activated. The storage chamber 150 may be charged with any suitable amount of propellant 154 to pressurize the composition 152 to a desired pressure, such as, for example, within a range from about 5 psi to about 50 psi, from about 10 psi to about 40 psi, or from about 12 psi to about 30 psi. The propellant 154 may be any suitable gaseous propellant 154 that does not react with the composition 152 and that is suitable for topical application, preferably, pressurized air or nitrogen. In this exemplary embodiment, the reservoir 102 further comprises a dip tube 156 having a first end submersed within the composition 152 and a second end operably connected to the dispenser 159 for drawing the composition 152 from the first end to the second end and dispensing the pressurized flow via the dispenser 159 when it is activated.

Figure 3:
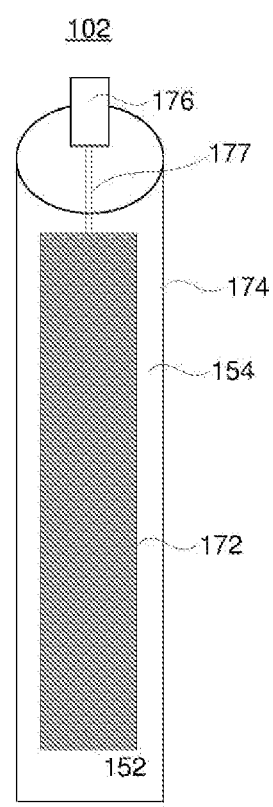
FIG. 3 shows an alternative exemplary embodiment of a reservoir charged with the composition that can be used with the exemplary device shown in FIG. 1.

In another exemplary embodiment, the reservoir 102 comprises a bag-on-valve system, an exemplary embodiment of which is shown in FIG. 3. The bag-on-valve system includes a flexible bag 172 holding a charge of the composition 152 within an interior chamber defined therein. The bag 172 changes size and shape as the pressure applied outwardly by its contents (and/or pressures applied to the external surface(s) of the bag 172) varies during use (e.g., as the contents of the bag 172 are dispensed). The bag 172 is preferably formed from a non-elastic material suitable for storing the composition 152. In an exemplary embodiment, the bag 172 is formed from two sheets of polymer-laminated aluminum sealed together along outer edges of the internal chamber. An opening of the bag 172 is operably connected (e.g., via a dip tube 177) to a dispenser 176 for dispensing a pressurized flow of the composition 152 from the interior chamber when the dispenser 176 is activated. The bag-on-valve system further comprises an external rigid canister 174 that does not vary in size or change shape in response to changing internal pressures during operation of the device 100. The external canister 174 is suitably sized and shaped to receive the bag 172 therein. In this embodiment, the bag 172 is inserted into the external canister 174 and the canister 174 is further charged with the propellant 154. The propellant 154 within the external canister 174 exerts pressure against exterior surfaces of the bag 172 to deform the size and shape of the bag 172 and/or pressurize the interior chamber of the bag 172. Therefore, the composition 152 stored within the interior chamber can be pressurized by the propellant 154 in the exterior canister 174 even though the composition 152 and the propellant 154 are maintained in separate chambers within the bag-on-valve system and do not intermix. Specifically, pressure from the propellant 154 pushes radially inward against the bag 172 compressing the composition 152 therein to generate propulsion for dispensing, via the dispenser 176, a pressurized flow of the composition 152 from the interior chamber of the bag 172 when the dispenser 176 is activated.

In an alternative embodiment, the external canister 174 may include a biasing mechanism (e.g., a spring, or an electronically controlled actuator controlled by the processing arrangement 112 to bias the piston towards an emptied configuration) therein for pushing against and exerting pressure onto exterior surfaces of the bag 172 to deform the size and shape of the bag 172. Similar to the propellant 154 discussed above, pressure exerted by the biasing mechanism pushes inward against the bag 172 compressing the composition 152 therein to generate propulsion for dispensing, via the dispenser 176, a pressurized flow of the composition 152 from the interior chamber of the bag 172 when the dispenser 176 is activated.

The device 100 further comprises an accumulator 108 defining an expandable chamber 109 for receiving the composition 152 from the reservoir 102. The reservoir 102 in this embodiment is fluidly connected by a series of conduits 103 and/or valves (e.g., including a supply valve 104, as will be further described below) to the accumulator 108 to deliver a pressurized flow of the composition 152 to the expandable chamber 109 of the accumulator 108. The expandable chamber 109 is biased towards a relaxed, deflated configuration in which the expandable chamber 109 is at its minimum size, and expands in response to a force applied against an interior surface of the chamber increasing its internal volume as pressurized material enters the expandable chamber 109. For example, the expandable chamber 109 is relaxed in a deflated configuration when unfilled. However, the expandable chamber 109 expands as it is charged with increasing amounts of the composition and/or with increasing pressure from the reservoir 102 to exert a force against an interior surface of the expandable chamber 109. As the composition and/or pressure is discharged from the expandable chamber 109, the force against the interior surface of the expandable chamber 109 dissipates and the chamber 109 contracts to return toward its deflated configuration. A stiffness of the expandable chamber 109 according to this embodiment is selected to permit expansion of the expandable chamber 109 as material from the reservoir 102 is supplied thereto so that the bias of the expandable chamber 109 exerts on the material therein a desired pressure at which the material is to be dispensed. For example, the expandable chamber 109 according to one exemplary embodiment is formed from materials having a stiffness such that volume of the expandable chamber 109 expands at a rate from about 1 KPa/μL to about 10 KPa/μL, or from about 3 KPa/μL to about 5 KPa/μL, as the expandable chamber 109 is filled with the composition 152 from the pressurized flow dispensed by the reservoir 102. The expandable chamber 109 of the accumulator 108 preferably has a capacity significantly smaller than that of the reservoir 102. For example, the accumulator 108 may have a maximum fill capacity, within operating pressures of the device 100, from about 1 μL to about 50 μL, from about 2 μL to about 30 μL or from about 5 μL to about 25 μL. Those skilled in the art will understand that this accumulator 108 and the expandable chamber 109 permit the device to maintain a pressure at which the composition is dispensed within a desired range even as the pressure in the reservoir 102 changes during use.

In some embodiments, only a portion of the accumulator 108 is formed from elastic material while in other embodiments the entire accumulator 108 is formed of elastic material. When the force against the elastic material is relieved, e.g., as the material in the elastic chamber is discharged and, consequently, the pressure within the expandable chamber 109 decreases, the elastic material returns under its natural bias toward its undeformed configuration. Suitable elastic materials may include, for example, natural or synthetic rubbers, saturated or unsaturated rubbers, elastomers, e.g., silicone elastomers, thermoplastic elastomers, etc.

In an alternative embodiment, the accumulator 108 comprises a piston forming a portion of an interior surface of the expandable chamber 109, and a biasing mechanism attached to the piston biasing the piston towards an emptied configuration, in which the piston is fully advanced such that the expandable chamber 109 is at its minimum size. The biasing mechanism may comprise a spring, compressed air exerting pressure against the piston, and/or an electronically controlled actuator controlled by the processing arrangement to bias the piston towards an emptied configuration. The piston is reversibly operable to advance or retract in response to changing amounts of the composition and/or the changing level of pressure within the expandable chamber 109. For example, the biasing mechanism is compressed in response to a force exerted against the piston by increasing amounts of the composition and/or increasing pressure within the expandable chamber 109 so that the piston is retracted increasing the size of the expandable chamber 109. As the force against the piston is relieved, e.g., by discharging the composition and/or pressure from the accumulator 108, the biasing mechanism extends and returns toward the piston emptied configuration.

The device 100 according to this embodiment includes a supply valve 104 disposed between the reservoir 102 and the accumulator 108 that reversibly opens and closes to regulate pressurized flow from the reservoir 102 to the accumulator 108. The supply valve 104 opens to allow the pressurized flow to pass therethrough into the accumulator 108, and closes to prevent pressurized flow from entering the accumulator 108. In some embodiments, the supply valve 104 is adjustable in predetermined increments. For example, the supply valve 104 may reversibly open and close in predetermined increments to incrementally increase or decrease a flow rate and/or a pressure of the pressurized flow passing through the supply valve 104 into the accumulator 108.

The device 100 according to this embodiment also comprises a pressure sensor 106 monitoring pressure of the composition 152 in the accumulator 108. The pressure sensor 106 may be positioned in any location suitable for detecting a fluid pressure of the composition in the accumulator 108, for example, the pressure sensor 106 may be located within the accumulator 108 or may be external to the accumulator 108 (e.g., monitoring pressure by detecting a level of expansion of the expandable chamber 109). More particularly, the pressure sensor 106 may be mounted onto an interior wall of the expandable chamber 109 of the accumulator 108. The pressure sensor 106 detects changes in pressure and generates pressure data corresponding to a pressure of the composition in the accumulator 108. In some embodiments, the pressure sensor 106 may continuously monitor (at any desired frequency and/or rate) and generate pressure data corresponding to pressure of the composition in the accumulator 108 over any desired period of time.

The device 100 further comprises an orientation detector 158 monitoring an orientation of the device 100 (e.g., relative to vertical) when it is held by a user. The orientation detector 158 may comprise any suitable device(s) for detecting an orientation of the device 100 such as accelerometers, etc. to determine, for example, when the device 100 is held in a flow restricted configuration during which (depending on the design of the reservoir) an opening of the dip tube 156 may not be within the fluid in the reservoir 102. At such times, as would be understood by those skilled in the art, the device 109 may be unable to supply fluid to the accumulator 108 and thus, if the expandable chamber 109 is emptied before the device 100 is returned to an upright position, dispensing of the composition may be temporarily unavailable. The orientation detector 158 may detect changes to the position and/or orientation of the device relative to gravity and generate orientation data corresponding to the positioning and/or orientation of the device 100. As would be understood by those skilled in the art, data from the orientation detector 158 may be used to control the dispensing of composition, to provide feedback to the user to suggest repositioning the device 100, etc.

The pressure sensor 106, the orientation detector 158, and/or the supply valve 104 are operably connected to a processing arrangement 112 executing instructions stored on a computer-accessible medium 114. The processing arrangement 112 in this embodiment receives and analyzes pressure data received from the pressure sensor 106 and controls the supply valve 104. The processing arrangement 112 may also receive and analyze orientation data received from the orientation detector 158 to further control the supply valve 104. It is contemplated that the processing arrangement 112 and the computer-accessible medium 114 may be positioned anywhere within or external to the device 100. The processing arrangement 112 may be, e.g., entirely or a part of, or include, but is not limited to, a computer/processor that can include, e.g., one or more microprocessors, and use instructions stored on a computer-accessible medium 114 (e.g., memory storage device). The computer-accessible medium 114 may, for example, be a non-transitory computer-accessible medium containing executable instructions therein. A storage arrangement may be provided separately from the computer-accessible medium 114, which may provide the instructions to the processing arrangement 112 to configure the processing arrangement 112 to execute certain exemplary procedures, processes and methods.

The device 100 further includes a deposition arrangement 110 for dispensing the composition from the accumulator 108 as a pressurized spray. The deposition arrangement 110 is fluidly connected by a series of conduits 103 and/or valves to the accumulator 108 for obtaining the composition from the accumulator 108 and dispensing the pressurized composition. The deposition arrangement 110 in this embodiment may include, for example, a sprayer (e.g., an electronic sprayer or airbrush sprayer), a drop control device, or any other suitable application device for dispensing a pressurized composition via the deposition arrangement 110. In one example, the deposition arrangement 110 includes one or more suitable nozzles (and/or valves, atomizers, etc.) for dispensing the composition from the accumulator 108 as a pressurized spray of droplets to form a uniform or substantially uniform thin layer of coverage on the skin. In some embodiments, the deposition arrangement 110 is operably connected to the accumulator 108 to dispense a pressurized spray of the composition from the accumulator 108 without any pressure sources between the accumulator 108 and the deposition arrangement 110. The pressurized spray in this exemplary embodiment is propelled by the pressure of the composition obtained from the accumulator 108 and does not require any additional pressure sources before dispensing via the deposition arrangement 110.

The nozzle may be any suitable device for dispensing droplets of the composition under pressure as would be understood by those skilled in the art. In certain embodiments, the deposition arrangement 110 comprises multiple nozzles. The use of multiple nozzles can increase an overall rate at which the device 100 may apply the composition to the skin. For example, the deposition arrangement 110 may include 2 to 10 nozzles, 3 to 8 nozzles, or 4 to 6 nozzles, each nozzle being aimed differently so that the composition can be applied to multiple regions on the skin at the same time. In one exemplary embodiment, the deposition arrangement 110 includes 5 nozzles. The nozzle(s) may each comprise a valve operably connected to the processing arrangement 112 for dispensing the composition by rapidly opening and closing the valve to release a pulse of a pressurized spray droplets of the composition. In an exemplary embodiment, the deposition arrangement 110 is operably connected to a processing arrangement 112 executing instructions stored on a computer-accessible medium 114. The processing arrangement 112 may be further configured to direct and control dispensing of the composition from the accumulator 108 and through the deposition arrangement 110.

The device 100 further comprises a power source (not shown) providing power to control and operate the device 100. It is contemplated that the power source may be located anywhere within the device 100 or may alternatively be external to the device 100. In one exemplary embodiment, the power source is operably connected to the supply valve 104, the pressure sensor 106, the orientation detector 158, the processing arrangement 112 and/or the deposition arrangement 110. Those skilled in the art will understand that various known suitable sources of power may be used. For example, the power source may comprise a battery or a connection to an external source of power. In particular, the power source may comprise a rechargeable battery device.

Figure 4:
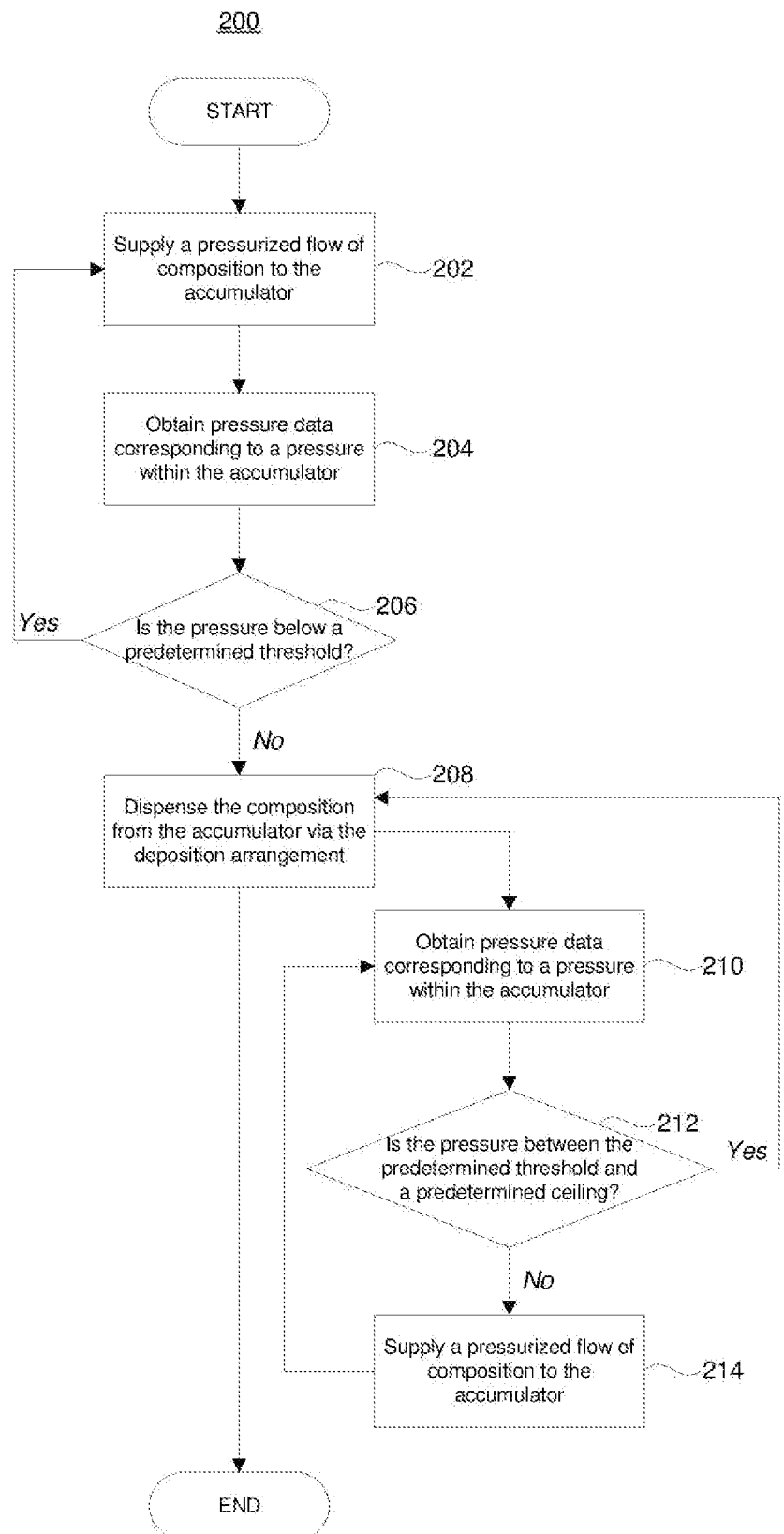
FIG. 4 shows an exemplary method for applying a composition to the skin of a user, according to an exemplary embodiment of the present application.

The present application also describes a method for dispensing a pressurized fluid composition. An exemplary method 200 is show in FIG. 4. When the device 100 is initially activated, the accumulator 108 may initially be unfilled and in a relaxed, unexpanded configuration. Steps 202 to 206 show an initial start-up stage for priming the accumulator 108 with a pressurized supply of the composition from the reservoir 102. In this embodiment, an initial supply of the composition is provided to fill the accumulator 108 with the composition until a desired pressure within the accumulator 108 is reached. For example, in step 202, a pressurized flow of the composition is provided to an expandable chamber 109 of an accumulator 108 via a supply valve 104. As discussed above, the pressurized flow is, in certain embodiments, dispensed from a reservoir 102 charged with a pressurized supply of the composition. The supply valve 104, which is disposed between the reservoir 102 and the accumulator 108, reversibly opens and closes to control the supply of the composition flowing therethrough to the accumulator 108. The processing arrangement 112 is operably connected to and directs the supply valve 104 to open and/or close as determined by the processing arrangement 112 to achieve and maintain the desired state of the accumulator 108. In this initial step 202, the processing arrangement 112 directs the supply valve 104 to open, allowing the pressurized flow from the reservoir 102 to fill the expandable chamber 109 of the accumulator 108 to a desired level.

As the pressurized flow is supplied to the accumulator 108, the pressure sensor 106 monitors and generates pressure data corresponding to the fluid pressure of the composition in the accumulator 108 (step 204). The pressure sensor 106 provides real-time or near real-time feedback of the pressure within the accumulator 108, as the expandable chamber 109 of the accumulator 108 fills with the composition. In step 206, the processing arrangement 112 receives the pressure data from the pressure sensor 106 and analyzes the pressure data to determine whether the accumulator 108 has been filled with the composition to a desired pressure. More specifically, the processing arrangement 112 analyzes the pressure data to determine whether the pressure within the accumulator 108 has reached or exceeded a predetermined threshold value. If the pressure within the accumulator 108 is below the predetermined threshold value, the processing arrangement 112 directs the supply valve 104 to remain open to continue to supply the pressurized flow to the expandable chamber 109 of the accumulator 108 (step 202). If the pressure within the accumulator 108 has reached or exceeded the predetermined threshold value, the processing arrangement 112 directs the supply valve 104 to move to a closed configuration to stop the pressurized flow from filling the accumulator 108. The predetermined threshold value is preferably selected to be a pressure below a pressure at which the composition is held in the reservoir 102. More particular, the predetermined threshold value is selected to be a pressure suitable for application to a biologic surface (after passing through the one or more nozzles of the deposition arrangement). For example, the predetermined threshold value may be selected from a range front about 3 psi to about 9 psi, from about 4 psi to about 7 psi, or preferably, about 5 psi. This initial start-up stage (steps 202 to 206) may be performed continuously or may be incrementally iterated at a predetermined frequency or rate. For example, steps 202 to 206 may be iterated every 5 seconds, every 3 seconds, or every 1 second until the pressure within the accumulator 108 reaches or exceeds the predetermined threshold value.

Once the expandable chamber 109 of the accumulator 108 has been filled to the desired level, the device 100 is adequately primed for dispensing the composition via the deposition arrangement 110. The deposition arrangement 110 dispenses the composition, for example, as pressurized pulses or as a continuous pressurized stream of the composition. In step 208, the processing arrangement 112 receives instructions (e.g., based on a user interaction with an actuator or other control) and activates the deposition arrangement 110 to deliver the composition to the skin. The deposition arrangement 110 obtains the composition from the accumulator 108 and dispenses the composition via one or more nozzles, valves, and/or atomizers as a pressurized spray. In some embodiments, the deposition arrangement 110 dispenses the composition from the accumulator 108 to the skin without use of any additional pressure sources, as discussed above. In this exemplary embodiment, the deposition arrangement 110 dispenses the composition at a pressure that is substantially the same as the internal pressure of the accumulator 108, When multiple nozzles, valves and/or atomizers are used, the pressure of the composition dispensed by each may be the same or substantially the same as one another. Those skilled in the art will understand that, depending on the geometry and number of nozzles, etc. the pressure of the composition leaving the nozzles, etc. may be higher or lower than that of the composition leaving the accumulator 108 so that, the pressure of the composition leaving the accumulator 108 is controlled to achieve a desired pressure leaving the nozzles.

As discussed above, the deposition arrangement 110 may comprise one or more nozzle(s) each having a valve operably connected to the processing arrangement 112 for dispensing the composition by rapidly opening and closing the valve to release a pulse of a pressurized spray droplets of the composition. The valve(s) of the deposition arrangement 110 may rapidly open and close within 0.5 ms, within 0.3 ms, within 0.2 ms, or within 0.1 ms, to release a pressurized spray of the composition. Preferably, the pressurized spray has a pressure from about 3 psi to 20 psi, from about 4 psi to about 15 psi, or from about 5 psi to about 10 psi. The accumulator 108 may be suitably configured (e.g., having a size, shape, stiffness and/or pressure) such that a desired amount of the composition is dispensed during each pulse without use of any additional pressure sources. For example, each nozzle, or all of the nozzles within the deposition arrangement 110, collectively, may dispense during each pulse from about 1 nanoliters to about 50 nanoliters, from 2 nanoliters to about 25 nanoliters, from about 3 nanoliters to about 10 nanoliters or about 5 nanoliters of the composition.

As the deposition arrangement 110 dispenses pressurized pulses of the composition from the accumulator 108 to the keratinous substrate, pressure within the expandable chamber 109 of the accumulator 108 slowly dissipates. The device 100 may adjust the supply of composition from the reservoir 102 to maintain pressure of the expandable chamber 109 of the accumulator 108 within a desired range, as describes further below in steps 210 to 214. In steps 210 to 214, the processing arrangement 112 controls the supply valve 104 and the pressure sensor 106 in a feedback loop to maintain pressure within a desired range, regardless of change in elevation or temperature for the surrounding environment in which the device 100 is used.

In step 210, the pressure sensor 106 continues to monitor the pressure of the expandable chamber 109 as the deposition arrangement 110 dispenses the composition from the accumulator 108 to the skin. In step 212, the processing arrangement 112 receives the pressure data from step 210 and analyzes the pressure data to determine whether the pressure within the accumulator 108 is within a desired pressure range, in particular, between the predetermined threshold value discussed above, and a predetermined ceiling value. The predetermined ceiling value of this embodiment is less than a pressure of the reservoir 102. Moreover, the predetermined ceiling value is preferably selected within a predetermined margin of error, within which variabilities are not noticeable when applied to the skin of the user, and do not impact the aesthetic appearance of coverage provided by the composition as applied onto the skin. For example, the predetermined ceiling value may be within 1 psi to 5 psi from the predetermined threshold value. In one exemplary embodiment, the predetermined threshold value may be about 5 psi and the predetermined ceiling value may be about 7 psi. If the pressure within the accumulator 108 is within a range between the predetermined threshold value and a predetermined ceiling value, then the accumulator 108 does not require adjustments. However, if the pressure within the accumulator 108 falls below the predetermined threshold value, the processing arrangement 112 directs the supply valve 104 to re-open to re-supply the pressurized flow to the expandable chamber 109 of the accumulator 108 (step 214) and maintain the pressure of the accumulator 108 within the range between the predetermined threshold value and a predetermined ceiling value.

Figure 5:
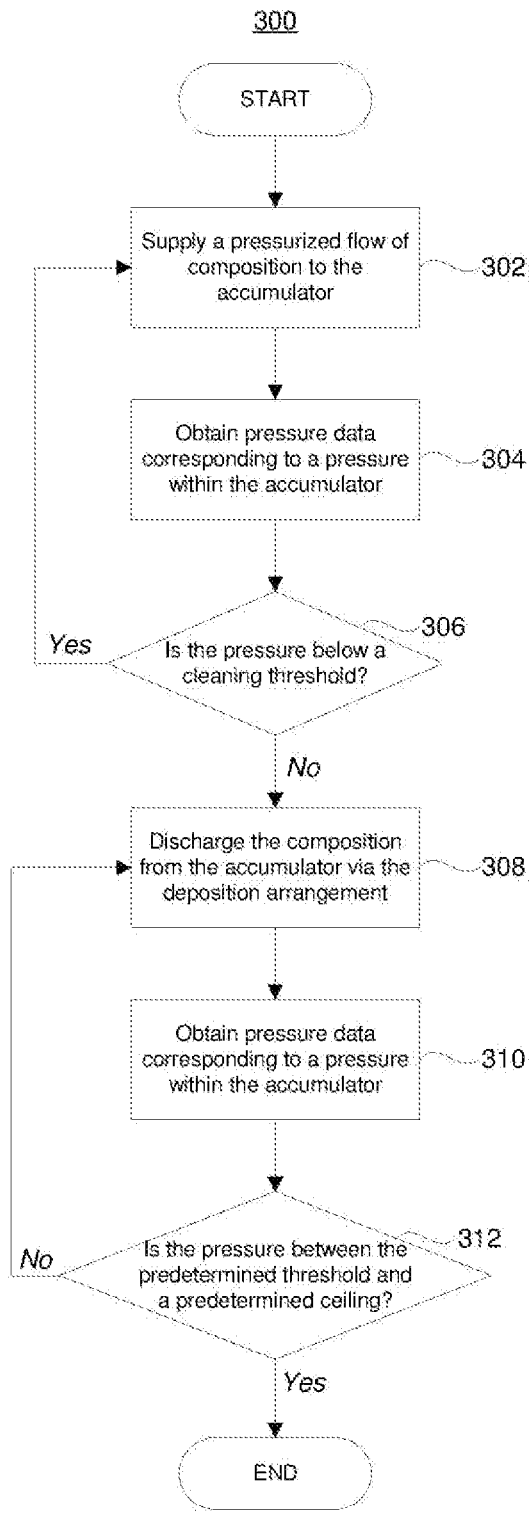
FIG. 5 shows an exemplary method for operating an exemplary device in a cleaning mode, according to an exemplary embodiment of the present application.

The present application also includes a method to operate the device 100 in a cleaning mode. An exemplary method 300 for cleaning the device 100 is show in FIG. 5. The device 100 may operate in cleaning mode at any suitable time. For example, the device 100 may operate in a cleaning mode when the device 100 is initially activated for use in a session or upon completion of a session. The device 100 may also operate in a cleaning mode in response to manual input by a user. The device 100 may diverge from normal operations, as exemplified in method 200, enter into a cleaning mode, as exemplified in method 300, and resume normal operations, i.e., continuing in method 200, after the device 100 has completed the cleaning mode. In one exemplary embodiment, when the device 100 is initially activated, the device 100 starts in the cleaning mode as shown in FIG. 5. In particular, the exemplary method 300 of the cleaning mode replaces steps 202 to 206 of method 200. After step 310 is completed, the device 100 may continue to step 208 within method 200 as described above.

Steps 302 and 304 are substantially similar to steps 202 and 204 described above. However, in step 306, the processing arrangement 112 receives pressure data from the pressure sensor 106 and analyzes the pressure data to determine whether the accumulator 108 has been sufficiently filled with the composition to reach a cleaning threshold value. The cleaning threshold value is selected to be a pressure higher than the predetermined threshold value and/or the predetermined ceiling value. The cleaning threshold value is preferably selected to be a pressure below the pressure of the reservoir 102 so that additional pressure sources are not necessary for operating the device 100 in the cleaning mode. In some embodiments, the cleaning threshold value is selected so that the deposition arrangement 110 dispenses the composition from the accumulator 108 at a pressure that provides force sufficient to dislodge obstructions, such as, for example, dried and caked-on composition, in the deposition arrangement 110. For example, the predetermined threshold value may be selected from a range from about 5 psi to about 20 psi, from about 6 psi to about 15 psi, or preferably, about 10 psi. Steps 302 to 306 may be performed continuously or incrementally iterated at a predetermined frequency or rate. For example, steps 302 to 306 may be iterated every 5 seconds, every 3 seconds, or every 1 second until the pressure within the accumulator 108 is sufficiently raised to exceed the cleaning threshold value.

In step 308, the deposition arrangement 110 discharges the composition from the accumulator 108 via one or more nozzles, valves and/or atomizers to dispense a pressurized pulse or pressurized flow of the composition. The deposition arrangement 110 may initially dispense the composition from the accumulator 108 at a pressure that meets or exceeds the cleaning threshold value, but slowly dissipate as the deposition arrangement 110 dispenses pressurized pulses of the composition from the accumulator 108. Preferably, the deposition arrangement 110 dispenses the composition from the accumulator 108 at the same pressure as the pressure within the expandable chamber 109 of the accumulator 108, without any additional pressure sources. In the cleaning mode, the deposition arrangement 110 may discharge the composition as a continuous pressurized flow, or as a pressurized pulse incrementally dispensed at a predetermined frequency or rate (e.g., every 5 seconds, every 3 seconds, or every 1 second) until the pressure within the accumulator 108 is restored to be within the range between the predetermined threshold value and the predetermined ceiling value. For example, in step 310, the pressure sensor 106 continues to monitor the pressure of the expandable chamber 109 of the accumulator 108 as the deposition arrangement 110 dispenses the composition from the accumulator 108. In step 312, the processing arrangement 112 receives pressure data from step 310 and analyzes the pressure data to determine whether the pressure within the accumulator 108 is within a desired pressure range, in particular, between the predetermined threshold value discussed above, and a predetermined ceiling value, for application of the composition to the keratinous substrate, if the pressure within the accumulator 108 is still in excess of the predetermined ceiling value, the device 100 continues to discharge the composition from the accumulator 108 via the deposition arrangement 110 until the desired pressure is reached, e.g., the pressure falling below the predetermined ceiling value. Once the pressures of the accumulator 108 falls below the predetermined ceiling value, the device 100 resumes operation within method 200, in particular, continues to steps 208 to 214, as discussed above. In some embodiments, the deposition arrangement 110 may comprises a plurality of nozzles that may each be individually activated through each iteration of steps 308 to 312. For example, the processing arrangement 112 may direct the deposition arrangement 110 to discharge the composition via a rotating series of individually activated nozzles until the pressure within the accumulator 108 is restored to be within the range between the predetermined threshold value and the predetermined ceiling value. The collective amount of composition continually dispensed by the deposition arrangement 110 in the cleaning mode may comprise a small portion of a total amount of composition initially charged within the reservoir 102 so the composition is not excessively wasted by the device 100 when operating in cleaning mode. Preferably, the accumulator 108 is suitably configured (e.g., having a suitable size, shape, stiffness and/or pressure) such that the collective amount of composition dispensed by the device 100 in cleaning mode is a small portion (e.g., less than 1%, less than 0.5%, less than 0.3%, or less than 0.1%) of the total amount of composition initially charged within the reservoir 102. For example, the deposition arrangement 110 dispenses in the cleaning mode a collective amount from about 1 microliter to about 50 microliters, about 3 microliters to about 25 microliters, or from about 5 microliters to about 20 microliters of the composition.

The increased cleaning pressure used in method 300 allows the device 100 to dispense the composition at an elevated pressure to assist unclogging of obstructions and/or to purge residual composition in air exposed portions of the deposition arrangement from prior use. The purging of fluid from air exposed portions of the deposition arrangement 110 clears the deposition arrangement 110 of old, air-exposed residual amounts of the composition from prior use, which can accumulate dirt, bacteria, mold and/or other undesirable contaminants during storage of the device 100 between uses. However, the increased cleaning pressure is preferably selected to be a pressure within the same operating pressure range during normal operation within method 200 before continuing use of the device 100 for application of the composition to a keratinous substrate.

In one exemplary embodiment, the reservoir 102 is a pressurized canister filled within the composition and a propellant. The pressurized canister may be initially charged with about 5 mL of the composition, which is gradually depleted as the device 100 is continually used. The propellant in this embodiment is nitrogen and pressurizes the composition within the pressurized canister to a pressure from about 12 psi to about 30 psi. In particular, when the canister is filled to 5 mL, the nitrogen gas pressurizes the composition to a pressure about 30 psi. As the composition is discharged from the canister, the pressure is gradually reduced to about 12 psi, when the composition is completely emptied from the canister. Therefore, this exemplary pressurized canister can provide a pressurized flow of the composition having at least a pressure of 12 psi to the accumulator 108. As already discussed above, a first step in the cleaning mode is to supply a pressurized flow of the composition to the accumulator 108. In particular, the processing arrangement 112 directs the supply valve 104 to open and allow a pressurized flow of the composition to pass therethrough to fill and expand the expandable chamber 109 of the accumulator 108. The processing arrangement 112 monitors, via the pressure sensor 106, the pressure of the expandable chamber 109 and directs the supply valve 104 to close once a desired pressure within the expandable chamber 109 is reached. In this example, the supply valve 104 remains open until a pressure of about 12 psi is reached within the expandable chamber 109. The deposition arrangement 110 in this embodiment may include a plurality of nozzles, preferably 5 nozzles. In a cleaning mode, the processing arrangement 112 directs the deposition arrangement 110 to discharge the composition by activating a single nozzle and individually cycling through each of the plurality of nozzles for each iteration of steps 308 and 312 as discussed above. Each of the nozzles comprises a valve that rapidly opens and closes to release about a pulse of a pressurized spray droplets of the composition. In particular, each valve may open and close within about 0.2 ms to dispense about 5 nanoliters of the composition during each pulse. As the composition is discharged through each of the nozzles, pressure within the expandable chamber 109 of the accumulator 108 incrementally decreases. The processing arrangement 112 continues to cycle through the nozzles to discharge the composition until a desired pressure for normal operation of the device 100 is reached. In this example, the desired operating pressure is about 5 psi, and a collective amount of about 15 microliters of the composition may be dispensed in the cleaning mode.

The device 100 is capable of dispensing pressurized composition from the deposition arrangement 110 when it is held in any orientation, whether it is held in an upright configuration or in a flow restricted configuration so long as composition remains within the accumulator 108. The ability to operate the device 100 in any configuration, including a flow restricted configuration, can be useful to allow flexible manual manipulation of the device across different skin areas on the face of a user to access difficult to for application of the composition.

In one exemplary embodiment, the reservoir 102 comprises a storage chamber 150, a dispenser 159 and a dip tube 156 having a first end 157 submersed within and open to the composition 152 and a second end 161 operably connected to the dispenser 159 for drawing the composition from the first end 157 to the second end 161 and dispensing the pressurized flow via the dispenser 159 when it is activated. However, the dip tube 156 cannot draw the composition from the first end 157 to the second end 161 when the reservoir 102 is inverted or angled relative to the vertical so that the first end 157 of the dip tube 156 is no longer submersed in the composition 152. As discussed above, the orientation, i.e., whether or not the device 1001 is upright or inverted, may be detected by the orientation detector 158. The orientation detector 158 generates orientation data corresponding to the positioning and/or orientation of the device 100 relative to a vertical position. The processing arrangement 112 receives and analyzes the orientation data to determine whether the device 100 is being held at an orientation (e.g., inverted) in which the first end 157 is no longer submerged in the composition and closes the supply valve 104 when the orientation data indicates that the device 100 in such an orientation. Those skilled in the art will understand that the orientation detector 158 may employ any number of mechanisms in addition to or as an to an accelerometer to detect a condition in which the first end 157 is not submerged in the composition 152 including monitoring a level of fluid in the reservoir 102 and calculating a critical angle based on this amount at which the first end 157 is exposed, monitoring flow through the dip tube 156, etc. The orientation detector 158 monitors the positioning and/or orientation of the device 100 throughout its operation, including during methods 200 and 300 and provides the orientation data to the processing arrangement 112. In this exemplary embodiment, when the processing arrangement 112 determines that the device 100 is in a flow restricted configuration (e.g., when the first end 157 of the dip tube 156 is not submerged within the composition 152 within the reservoir 102), the supply valve 104 is closed and overrides steps 202, 214 and 302 discussed above. When the processing arrangement 112 determines that the device 100 is no longer in the flow restricted configuration (e.g., the device 100 resumes an upright configuration in which the first end 157 is submerged within the composition in the reservoir 102), the supply valve 104 is re-opened as determined in steps 202, 214 and 302 to refill the accumulator 108 as discussed above.

Although the supply valve 104 is closed when the device 100 is in a flow restricted configuration, the device 100 continues to dispense pressurized composition from the accumulator 108 via the deposition arrangement 110 so that use of the device 100 is not interrupted when the device 100 is inverted. The expandable chamber 109 of the accumulator 108 can be suitably sized to store an amount of the composition therein sufficient to permit the device 100 to continue to dispense the composition from the accumulator 108 via the deposition arrangement 110 during a predetermined period of time or over a predetermined number of pressurized pulses, even if the accumulator 108 does not receive any additional supply of the composition from the reservoir 102 during this time. Preferably, the accumulator 108 has a capacity for storing an amount of composition sufficient to continue dispensing the composition from the accumulator 108 via the deposition arrangement 110 over a predetermined period of time or for a predetermined number of pressurized pulses, without the pressure of the expanded chamber of the accumulator 108 falling below the predetermined threshold value or within predetermined margin of error, within which variabilities are not noticeable when applied to the skin, and do not impact the aesthetic appearance of coverage provided by the composition. For example, the predetermined margin (f error may be less than 2 psi, or preferably, less than 1 psi. For example, the device 100 may be capable of dispensing the composition from the accumulator 108 via the deposition arrangement 110, without any additional supply from the reservoir 102 or any additional pressure sources, for at least 15 seconds, at least 30 second, or at least 1 minute. As another example, the expandable chamber 109 of the accumulator 108 may be sized to be capable of dispensing the composition from the accumulator 108 via the deposition arrangement 110, without additional supply from the reservoir 102 for at least 50 pressurized pulses, at least 100 pressurized pulses, at least 300 pressurized pulses while maintaining the pressure of the expandable chamber 109 above the predetermined threshold within the predetermined margin of error.

The present invention will be further understood by reference to the following Example which is illustrative of the composition, form and method of producing the present invention. It is to be understood that many variations of composition, form and method of producing this would be apparent to those skilled in the art. The following Example, wherein parts and percentages are by weight unless otherwise indicated, are only illustrative.

EXAMPLE

Example I

Example I provides an exemplary embodiment of a device 100 for applying a fluid composition, in particular a pressurized fluid composition, as described above and illustrated in FIG. 1. A suitable fluid composition has a viscosity at or about 1 cP (e.g., water) at room temperature. It is also contemplated that the exemplary device of Example I may be used with a fluid composition that is more viscous than water. The exemplary device of Example I includes a constant pressure liquid source of the fluid composition to be dispensed by the device, set at 30 psi, acting as the reservoir 102. The liquid source feeds the fluid composition via rigid tubing acting as exemplary conduits 103 to a micro-valve (e.g., G300-G3001000 commercially available from TechElan, LLC) acting as the supply valve 104. The micro-valve is fluidly connected via a T-shaped connector to a pressure sensor transducer, acting as the pressure sensor 106, and an exemplary embodiment of the accumulator 108. The T-shaped connector is connected via additional rigid tubing to the pressure sensor transducer. In Example I, the pressure sensor transducer is a piezoresistive silicon pressure sensor, such as the board mounted pressure sensors commercially available from Honeywell International Inc. (e.g., sensors designated as SSCMLNT060PGAA5). The exemplary accumulator of Example I is an elastomer tubing, more specifically, silicone tubing. The exemplary accumulator has an elastic portion having a predetermined length that is not structurally supported by other components connecting thereto. The silicone tubing includes commercially available silicone rubber soft tubing, such as, for example, those having a hardness of at or about 50A durometer. A suitable silicone rubber soft tubing is commercially available from McMaster-Carr designated as 2124T3, having an inner diameter at or about $\frac{1}{16}$ inch, an outer diameter at or about $\frac{1}{8}$ inch, and a wall thickness at or about $\frac{1}{32}$ inches. The elastomer tubing is directly connected to a deposition valve, such as a micro-dispensing valve (e.g., G300-150300 commercially available from TechElan, LLC), acting as an exemplary embodiment of the deposition arrangement 110. The elastomer tubing is cut to length such that at or about 3.75 mm of length is the elastic portion of the elastomer tubing that is not structurally supported by the T-shaped connector or the deposition valve. The exemplary supply and deposition valves in Example I are connected to and operably controlled by an exemplary processing arrangement (e.g., LabVIEW system commercially available from National Instruments) according to the following steps:

A) Start. Open deposition valve for 1 microsecond.
B) Evaluate pressure detected by the pressure sensor:
   If the pressure detected by the pressure sensor is less than 5 psi, then close the deposition valve and open the supply valve for 1 microsecond. Wait 1 microsecond, and return to "Start" in Step A.
   If pressure is greater than 5 psi, return to "Start" in Step A.

The prototype of the exemplary device of Example I was constructed and demonstrated full functionality in applying a pressurized fluid composition to a substrate at a constant or substantially constant pressure of about 5 psi.

The invention described and claimed herein is not to be limited in scope by the specific embodiments herein disclosed since these embodiments are intended as illustrations of several aspects of this invention. Any equivalent embodiments are intended to be within the scope (if this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A handheld device, comprising:
   a reservoir configured to store a fluid topical composition comprising a suspension of particulate materials in a topical carrier for modifying appearance of a keratinous surface and to dispense a pressurized flow of the composition;
   an accumulator including an expandable chamber in fluidly communication with the reservoir, the expandable chamber being biased towards a deflated configuration so that, when filled with the composition the chamber expands against this bias applying pressure to the composition stored therein;
   a supply valve between the reservoir and the accumulator regulating the flow of the composition from the reservoir to the accumulator;
   a pressure sensor generating pressure data corresponding to a pressure of the composition in the accumulator;
   a processing arrangement receiving the pressure data from the pressure sensor, analyzing the pressure data to determine whether the pressure in the accumulator is above a predetermined threshold value and controlling the supply valve to maintain the pressure of the accumulator within a range between the predetermined threshold value and a predetermined ceiling value; and
   a deposition arrangement fluidly connected to an outlet of the accumulator, and the deposition arrangement configured to dispense the composition from the accumulator under control of the processing arrangement as a pressurized spray of droplets that form a thin layer of the composition covering an area on the keratinous surface, wherein the pressurized spray dispensed by the deposition arrangement is propelled by the pressure from the accumulator.

2. The handheld device of claim 1, wherein at least a portion of a wall of the expandable chamber is formed from an elastic material.

3. The handheld device of claim 2, wherein the elastic material comprises a silicone elastomer.

4. The handheld device of claim 2, wherein the expandable chamber is entirely formed form an elastic material.

5. The handheld device of claim 1, wherein the accumulator comprises a piston forming a portion of the interior surface of the chamber, and a spring biasing the piston towards the deflated configuration.

6. The handheld device of claim 1, wherein an increase in the pressure of the accumulator expands a volume of the chamber at a rate from about 3 KPa/µL to about 5 KPa/µL.

7. The handheld device of claim 1, wherein the predetermined ceiling value is less than a pressure of the reservoir.

8. The handheld device of claim 1, wherein the pressure of the reservoir ranges from about 12 psi to about 30 psi.

9. The handheld device of claim 1, wherein the reservoir comprises a storage chamber charged with the composition and a propellant, and a dip tube through which the composition is dispensed from the storage chamber.

10. The handheld device of claim 1, wherein the reservoir has a volume of no more than 15 ml.

11. The handheld device of claim 1, wherein the predetermined threshold value is about 5 psi.

12. The handheld device of claim 11, wherein the predetermined ceiling value is about 7 psi.

13. The handheld device of claim 1, wherein the deposition arrangement comprises at least one nozzle configured to dispense a pressurized pulse of the composition from the accumulator.

14. The handheld device of claim 13, wherein the nozzle is an atomizer nozzle configured to dispense a pressurized spray of droplets of the composition from the accumulator.

15. The handheld device of claim 1, wherein the pressurized spray of droplets form a thin layer of the composition covering an area on the surface.

16. The handheld device of claim 1, wherein the deposition arrangement dispenses the composition from the accumulator as pressurized pulses at a predetermined frequency, wherein each pressurized pulse deposits a layer of the composition covering an area on the surface.

17. The handheld device of claim 1, further comprising:
   an orientation detector monitoring an orientation of the device to generate orientation data corresponding to the orientation of the device, wherein the processing arrangement further receives the orientation data from the orientation detector and controls dispensing of the composition based on the orientation data.

18. The handheld device of claim 1,
   wherein the deposition arrangement comprises a plurality of nozzles, each nozzle comprising a valve operably connected to the processing arrangement, and
   wherein the processing arrangement controls dispensing of the composition by directing each of the valves to rapidly open and close to release a pulse of pressurized spray droplets of the composition.

19. The handheld device of claim 1, wherein the topical carrier is a liquid or a viscous fluid.

20. A method for dispensing a topical composition, comprising:
   supplying, via a supply valve, a pressurized flow of the composition to an accumulator including an expandable chamber therein, the chamber being biased towards a deflated configuration so that, when filled with the composition the chamber expands against this bias applying pressure to the composition stored therein, wherein the composition comprises a suspension of particulate materials in a topical carrier;

generating, by a pressure sensor, pressure data corresponding to a pressure of the composition in the accumulator;

analyzing, by a processing arrangement, the pressure data received from the pressure sensor to determine whether the pressure in the accumulator is above a predetermined threshold value and to control the supply valve to maintain the pressure of the accumulator within a range between the predetermined threshold value and a predetermined ceiling value; and dispensing, by a deposition arrangement fluidly connected to an outlet of the accumulator, the composition from the accumulator under control of the processing arrangement as a pressurized spray of droplets that form a thin layer of the composition covering an area on the keratinous surface, wherein the pressurized spray dispensed by the deposition arrangement is propelled by the pressure from the accumulator.

21. The method of claim 20, wherein the deposition arrangement is inverted during at least a portion of the dispensing step.

22. The method of claim 20, wherein the topical carrier is a liquid or a viscous fluid.

* * * * *